(12) United States Patent
Fletcher

(10) Patent No.: US 8,221,360 B2
(45) Date of Patent: Jul. 17, 2012

(54) MEDICATION CLIP

(75) Inventor: Michael J. Fletcher, Queensland (AU)

(73) Assignee: Rewall Pty Ltd., Queensland (AU)

( * ) Notice: Subject to any disclaimer, the term of this patent is extended or adjusted under 35 U.S.C. 154(b) by 263 days.

(21) Appl. No.: 11/727,457

(22) Filed: Mar. 27, 2007

(65) Prior Publication Data

US 2007/0173775 A1 Jul. 26, 2007

Related U.S. Application Data

(63) Continuation-in-part of application No. PCT/AU2005/001642, filed on Oct. 24, 2005.

(30) Foreign Application Priority Data

Nov. 5, 2004 (AU) ................................ 2004/906359
Mar. 27, 2006 (AU) ................................ 2006/901552

(51) Int. Cl.
*A61M 5/00* (2006.01)
(52) U.S. Cl. ........................................ 604/232; 604/234
(58) Field of Classification Search ................. 604/173, 604/191, 197, 232, 234, 233, 235
See application file for complete search history.

(56) References Cited

U.S. PATENT DOCUMENTS

| | | | |
|---|---|---|---|
| 1,678,991 A * | 7/1928 | Marschalek | 604/220 |
| 2,627,269 A | 2/1953 | McGregor | |
| 5,290,261 A * | 3/1994 | Smith et al. | 604/234 |
| 5,554,134 A * | 9/1996 | Bonnichsen | 604/240 |
| 6,234,994 B1 | 5/2001 | Zinger | |
| 6,361,193 B1 * | 3/2002 | Gabrius et al. | 362/365 |
| 6,511,030 B1 * | 1/2003 | Kelley | 248/309.1 |
| 6,681,946 B1 * | 1/2004 | Jansen et al. | 215/249 |
| 2002/0007155 A1 * | 1/2002 | Freund et al. | 604/232 |
| 2002/0083564 A1 | 7/2002 | James | |
| 2003/0073958 A1 * | 4/2003 | Pond | 604/232 |
| 2003/0233067 A1 | 12/2003 | McIntosh et al. | |
| 2004/0092872 A1 * | 5/2004 | Botich et al. | 604/110 |

FOREIGN PATENT DOCUMENTS

WO WO 2005/011781 A1 2/2005

OTHER PUBLICATIONS

Supplementary European Search Report dated Apr. 20, 2010. issued in EP 05797109.5, 6 pages.

* cited by examiner

*Primary Examiner* — Kevin C Sirmons
*Assistant Examiner* — Brandy C Scott
(74) *Attorney, Agent, or Firm* — Rothwell, Figg, Ernst & Manbeck, P.C.

(57) ABSTRACT

A disposable clip (10) is used to releasably attach an ampoule (13) to a syringe (11). The clip (10) includes an ampoule engaging portion (19) and a syringe engaging portion in the form of a recess (17). The ampoule engaging portion (19) comprises a compressible projection which is inserted into the neck (21) of the ampoule (13). The ampoule engaging portion (19) is thereby compressed and frictionally engages the inside of the neck (21) to secure the ampoule (13) firmly to the clip (10). The clip (10) does not obscure the label on the ampoule (13).

4 Claims, 12 Drawing Sheets

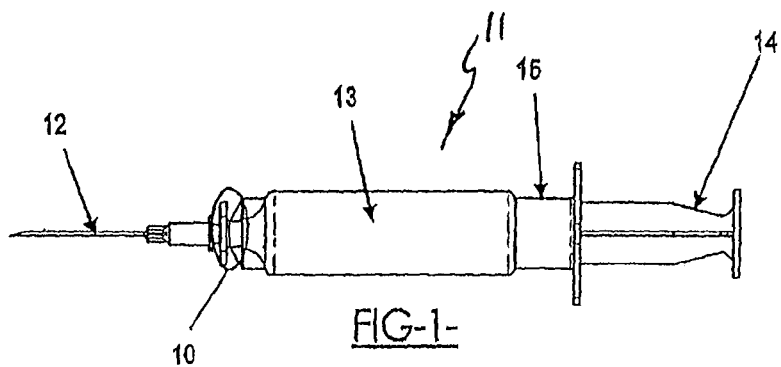
FIG-1-
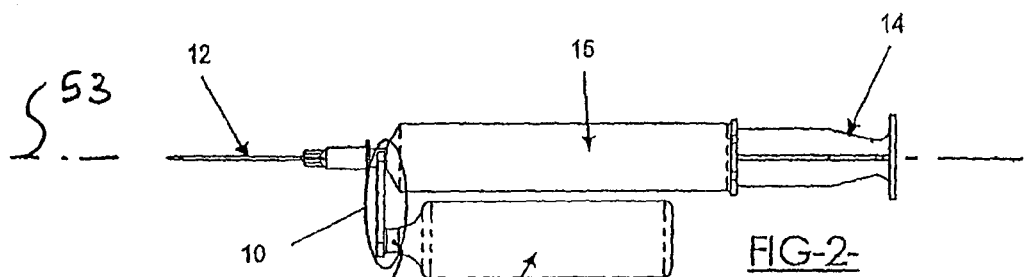
FIG-2-
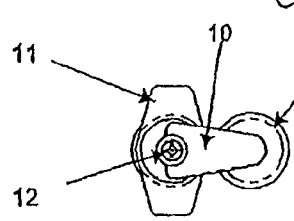
FIG-3-
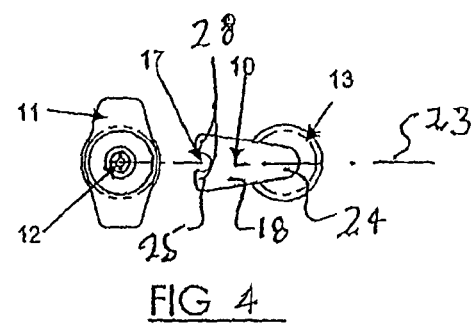
FIG 4
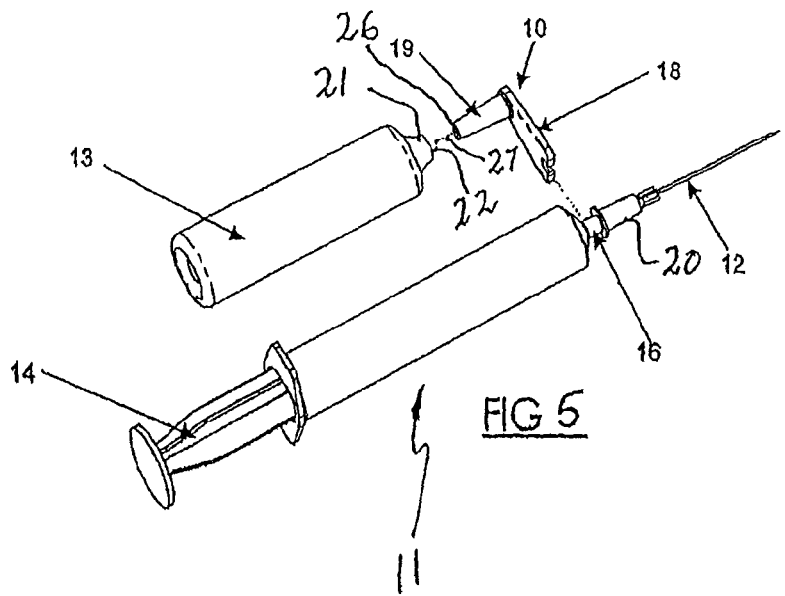
FIG 5

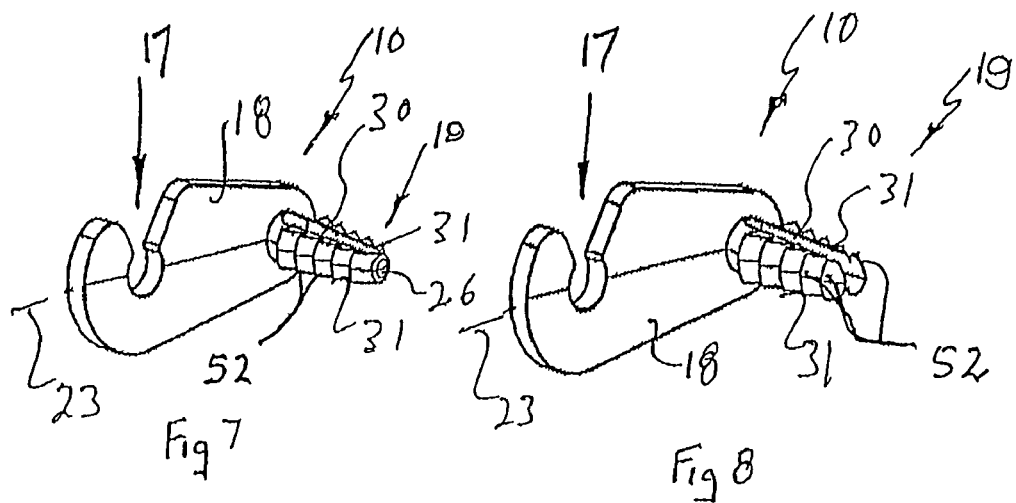
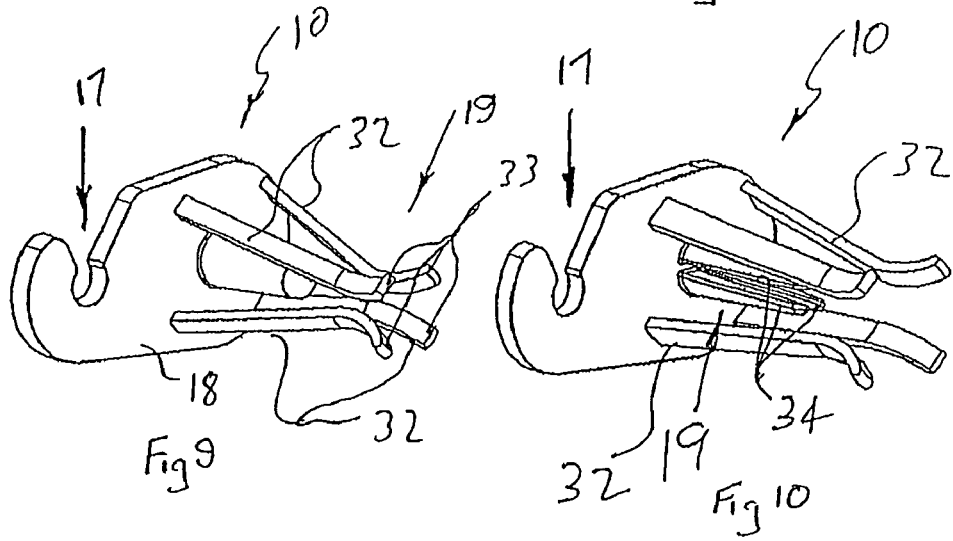
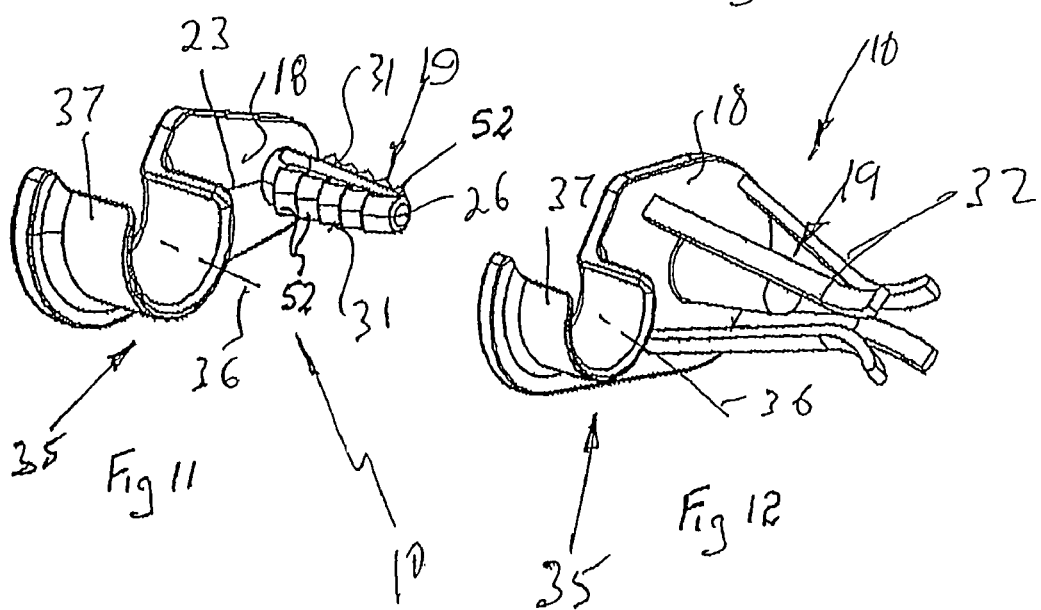

MEDICATION CLIP

RELATED APPLICATION

This application is a continuation-in-part of international patent application PCT/AU2005/001642 filed on Oct. 24, 2005, which claims priority from Australian patent application 2004/906359 filed on Nov. 5, 2004, and this application also claims the benefit of priority to Australian patent application 2006/901552 filed Mar. 27, 2006, the entire contents of each application are incorporated herein by reference.

FIELD OF THE INVENTION

The present invention relates to an improved clip for securing a medication ampoule to a syringe. The ampoule is typically a sealed glass vial or bulb used to hold medication, such as a hypodermic solution.

BACKGROUND OF THE INVENTION

Medication errors, such as Preventable Adverse Drug Reaction Events (ADE's), commonly occur in hospitals and in emergency care situations, and often have tragic consequences. Such errors include administration of the wrong drug, drug overdoses, and overlooked drug interactions and allergies.

More than one million serious medication errors occur every year in U.S. hospitals alone. According to a 1999 Institute of Medicine (IOM) report, medication errors alone contribute to 7,000 deaths annually. Medication errors also result in approximately 250,000 non-fatal injuries each year (Harvard Medical Practice Study). Preventable injuries caused by adverse reactions to drugs increased hospital costs by US$4,700 per admission (Journal of the American Medical Association) in the United States. Furthermore, this figure excludes other important costs of medication errors, such as malpractice insurance premiums, and losses in worker productivity.

One common cause of medication errors is poor identification of syringes in which medication has already been drawn-up. Prepared dosages, already drawn up into syringes, are used often in medical emergency situations and also in timetabled events such as surgery, where trays of medication needed over the course of the surgery are prepared before the surgery begins and are laid out on trays.

Of all medications, intravenous medications are one of the most difficult medications to identify once they have been drawn up into a syringe. Almost all intravenous medications appear as a clear liquid when viewed through a syringe sidewall with virtually no way of distinguishing between medications once drawn up.

It is therefore desirable for the ampoule from which the medication was drawn to be placed with the syringe, so that the type and/or intended dosage of medication can be ascertained, if necessary, from the label on the ampoule. It is common practice for an ampoule to be affixed directly onto a syringe using adhesive tape. (For example, the Queensland Ambulance Service Clinical Practice Manual instructs its members to use adhesive tape to attach the used glass ampoule to the syringe.) This practice has the disadvantage that the measurement indicators (dose markers) on the syringe body are often obscured, affecting the user's ability to read the dosage that has been drawn up into the prepared syringe. The portion of the label facing the syringe is also obscured. Another disadvantage of using adhesive tape to attach a used ampoule to the syringe is that the exposed jagged broken neck of the ampoule poses a risk of a sharps injury.

U.S. Pat. Nos. 5,290,261 and 2,627,269 each disclose clips for mounting an ampoule to a syringe. The device of U.S. Pat. No. 5,290,261 includes a socket that receives an ampoule, and a ring that surrounds the syringe. The socket and associated ring will only fit one size ampoule and syringe. The device of U.S. Pat. No. 2,627,269 has a basket that holds an ampoule. Again, the basket is designed for a particular size of ampoule. This device also has a relatively complex metal construction, and is therefore expensive to manufacture.

International patent application PCT/GB2004/003135 (WO 2005/011781) discloses a medical needle system having two cylinders. One cylinder is used to store the body of the syringe, and the other cylinder receives both a needle assembly and vial or ampoule. This system also has the disadvantage that it is intended for use only with syringes and vials of predetermined diameters. It is also relatively complex and therefore expensive to manufacture.

US patent application no. 2002/0083564 describes a clip for securing a vial to a syringe. The integrally formed flexible plastic clip comprises two juxtaposed c-shaped clips joined by a bridge, each clip being adapted to be snap-fitted to a syringe and vial, respectively. Yet again, the clip is intended for use only with syringe and vial of a predetermined size.

A serious disadvantage of all the prior art clips described above is that the portions of the clips which hold or secure the ampoule obscure the label on the ampoule to some degree. This renders it difficult, if not impossible, to read the label while the ampoule is attached to the syringe, and therefore increases the risk of administering the wrong drug or the wrong dosage.

OBJECT OF THE INVENTION

It is the object of the present invention to provide an improved clip for securing a medication ampoule to a syringe, which overcomes or substantially ameliorates at least one of the above disadvantages.

SUMMARY OF THE INVENTION

There is disclosed herein a clip for securing a medication ampoule to a syringe. The ampoule has an opening in a neck portion thereof, and the clip includes an ampoule engaging portion adapted to be received within the neck portion to thereby attach the ampoule to the clip.

Unlike prior art devices which engage the outside of the medication ampoule, the clip of the present invention engages within the ampoule, namely by having an ampoule engaging portion which is inserted into the opening of the medication ampoule. This gives rise to several advantages, including:

(a) as the clip engages the inside of the ampoule, it is suitable for use with all sizes and types of medication ampoules;
(b) as the clip engages the inside of the ampoule, it doesn't obscure important drug information on the label of the ampoule;
(c) due to the resting position of broken/jagged edge of glass ampoule against the body of the clip, the risk of a sharps injury is minimized.

Typically, the clip includes a base, which may be substantially planar and made of resiliently flexible plastics material, and the ampoule engaging portion is an integrally formed projection which preferably extends substantially perpendicularly from the plane of the base.

The projection is preferably resiliently compressible, and is adapted to engage the neck portion in an interference fit. This also assists in sealing the opening of the ampoule. It may be bifurcated along its length and/or it may be provided with a ridged outer surface for gripping the inside of the neck portion.

The clip may also be provided with a plurality of resiliently flexible finger portions extending from the base and spaced around the projection, the finger portions being adapted to grasp the external surface of the neck portion when the projection is inserted into the neck portion.

In another embodiment, the projection has a plurality of resiliently flexible extensions affixed to its distal end, and spaced circumferentially around the projection. The extensions have a rest configuration wider than the diameter of the opening, so that upon insertion of the projection through the opening, the extensions are compressed while passing through the neck portion but expand against the inside of the ampoule.

The base of the clip suitably includes a syringe engaging portion for releasably attaching the clip to the syringe. The syringe engaging portion may be a recess in the base which is shaped and dimensioned to receive a portion of the syringe therein in an interference or snap fit. This is normally a tip portion of the syringe of reduced diameter.

Alternatively, the syringe engaging portion may be a recess in the base which is shaped and dimensioned to receive a base portion of a needle assembly fitted to the syringe, in an interference or snap fit.

Preferably, the base includes a recess having two portions for receiving a tip portion of the syringe and a base portion of the needle assembly, respectively.

In an alternative embodiment, the syringe engaging portion is an arcuate socket within which the body of the syringe can locate in a snug or snap fit.

In yet another alternative embodiment, the clip is fixed to the syringe.

The base may be provided with two ampoule engaging portions spaced apart on the base, and the syringe engaging portion is located intermediate the two ampoule engaging portions.

In another embodiment, the syringe includes a syringe body, a needle mounting attachable to the syringe body and a needle fixed to and extending from the needle mounting, and the clip base is integrally formed with or fixed to said needle mounting.

There is also disclosed herein a method of securing a medication ampoule to a syringe using a clip having an ampoule engaging portion, comprising the steps of: inserting the ampoule engaging portion into an opening of the medication ampoule; and attaching the clip to the syringe.

Embodiments of the invention will now be described by way of example with reference to the accompanying drawings.

BRIEF DESCRIPTION OF THE DRAWINGS

FIG. 1 is a side view of a syringe and ampoule releasably attached by a clip according to a first embodiment;

FIG. 2 is a plan view of the syringe, ampoule and clip of FIG. 1;

FIG. 3 is an end view of the syringe, ampoule and clip of FIG. 1;

FIG. 4 is an end view of the syringe, ampoule and clip of FIG. 1 with the clip detached from the syringe;

FIG. 5 is an exploded isometric view of the syringe, ampoule and clip of FIG. 1;

FIGS. 7 to 12 are isometric views of modifications of the clip of FIG. 1.

DETAILED DESCRIPTION OF EMBODIMENTS OF THE INVENTION

Figure 6:
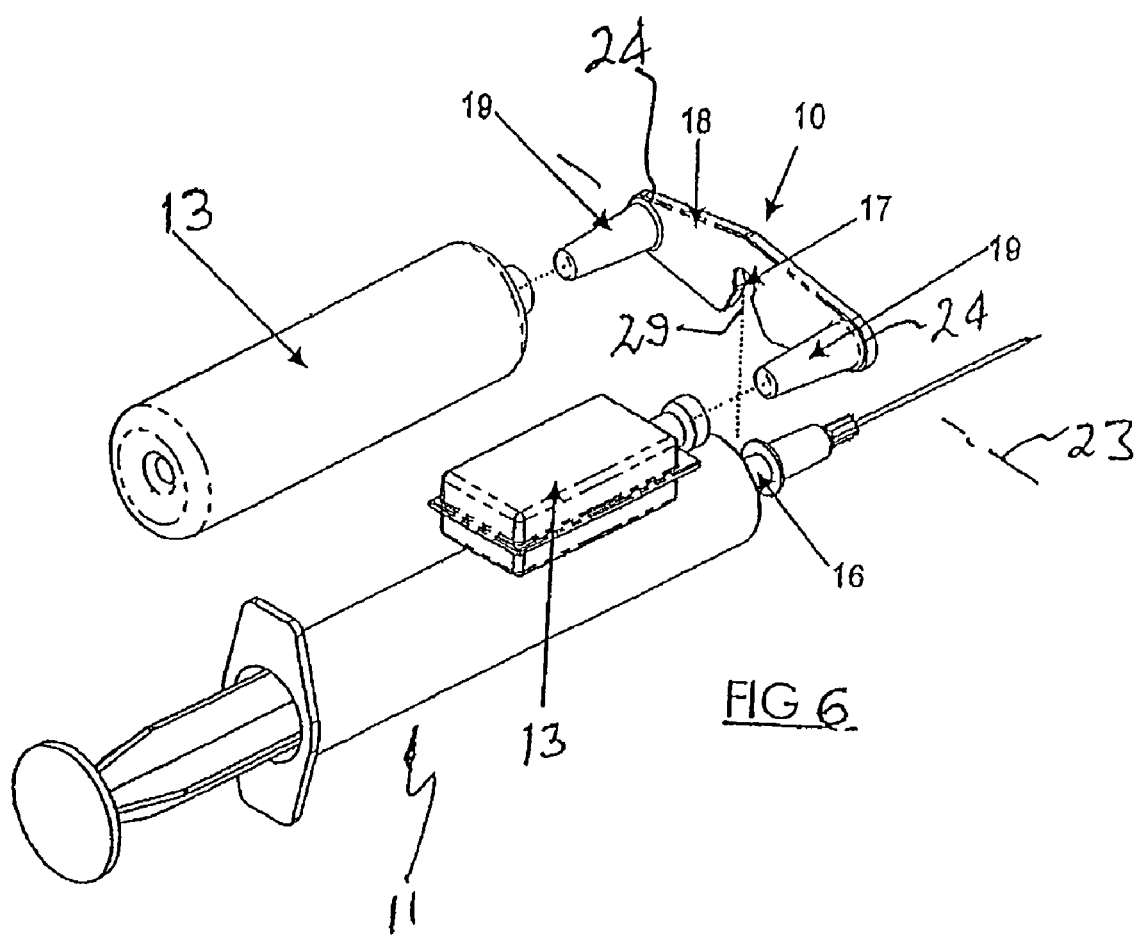
FIG. 6 is an exploded isometric view of a modification of the clip of FIG. 1 together with a syringe and two ampoules.
Figure 13:
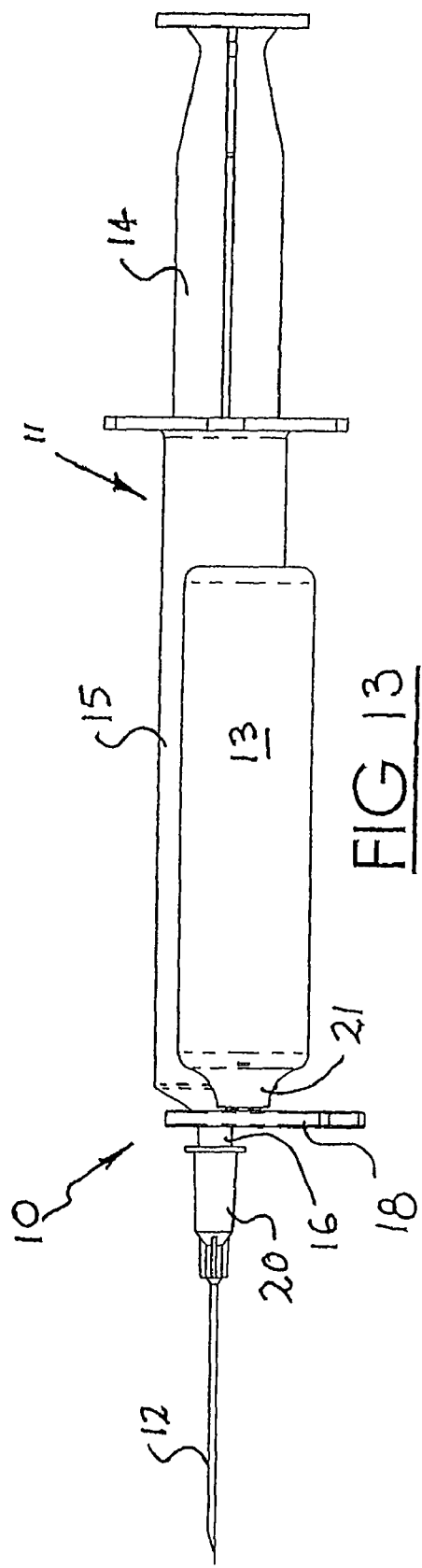
FIG. 13 is a side view of an another embodiment of the clip of this invention, with a syringe and ampoule secured thereto.
Figure 14:
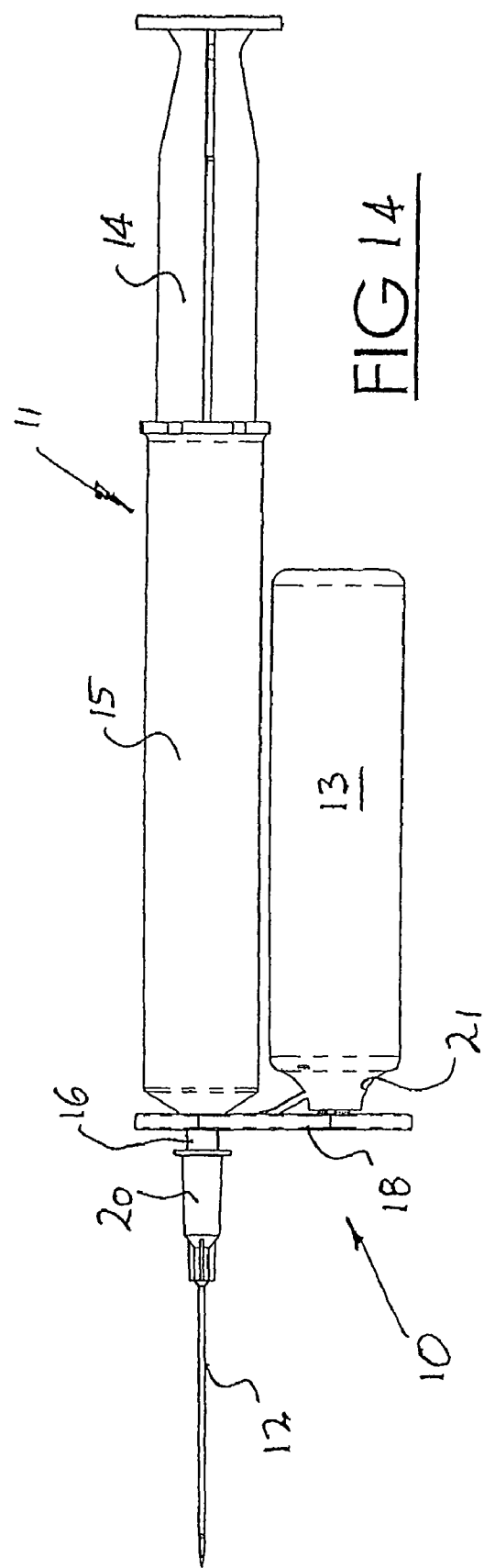
FIG. 14 is a plan view of the clip, ampoule and syringe of FIG. 13.

FIGS. 1 to 5 of the accompanying drawings depict schematically a first embodiment of a clip 10 for securing an ampoule 13 to a syringe 11. Typically the clip 10 is disposable, and is integrally formed from moulded plastics material, and more particularly from resiliently flexible plastics material.

The syringe 11 includes a hollow or cylindrical body 15 terminating at its forward end with a tip 16 of reduced diameter. The tip 16 frictionally engages the needle base 20 so that the needle 12 is secured to the tip 16. A plunger 14 is slidably located in the body 15 and is movable relative thereto to draw liquid into the body 15 and to expel liquid through the needle 12. Typically in use, the syringe 11 would be operated to withdraw liquid from within the ampoule 11, and then inject the liquid.

The ampoule 13 may be formed of glass or plastics, and includes a neck 21 having an opening 22.

The clip 10 includes a generally planar base 18 that is elongated so as to have a longitudinal axis 23. The base 18 has opposite end portions 24 and 25, with the end portion 25 being provided with an ampoule engaging portion 19. In this embodiment the portion 19 is a frusto-conical projection that tapers from the base 18 to its free end 26. The portion 19 has a longitudinal axis 27 that is generally normal to the axis 23 so that the portion 19 extends generally normal to the base 18.

In operation of the clip 10, the portion 19 is inserted into the opening 22 of the ampoule 13. As the portion 19 is urged into engagement with the neck 21, it is resiliently compressed by the neck 21 and fictionally engages the internal surfaces of the neck 21, i.e. in a snug or interference fit. In this manner, the ampoule 13 is mounted to the clip 10 securely, yet releasably.

The base 18 of the clip 10 comprises two resilient arms 28 defining a recess 17 between them, as shown in FIG. 4, used to attach the clip to the tip 16 of the syringe 11. The tip 16 is received within the recess 17 in an interference or snap fit as the arms 28 deflect apart to receive the tip 16 in the recess 17, and thereafter the arms 28 retain the tip 16 releasably secured in the recess 17.

Preferably, the edge of each arm 28 around the opening 17 is provided with a lip or projection that aids in retaining the tip 16 in the recess 17.

Preferably, the opening of the recess 17 faces away from the portion 19.

A modified version of the clip is shown in FIG. 6. In the embodiment of FIG. 6, the clip 10 is provided with a pair of ampoule engaging portions 19 for releasably attaching two ampoules 13 to the syringe 11. In this embodiment, the portions 19 are located at opposite end portions 24 of the base 18, with the recess 17 located therebetween. In this embodiment, the recess 17 extends away from the longitudinal axis 23, and has a tapered entrance passage 29.

FIGS. 7 to 12 illustrate further modifications of the clip. In the embodiment of FIG. 7, the portion 19 is still frusto-conical in overall configuration, but is bifurcated so as to have a central longitudinal slot 30 located between a pair of arms 31. The arms 31 are joined at the free end 26. The arms 31 are each provided with a plurality of barbs or detents 52 to aid in retaining the portion 19 in the neck 21.

In the embodiment of FIG. 8, the arms 31 are not joined at the free end 26. In use, the arms 31 are resiliently deflected together when the prong 19 is inserted in the neck 21.

In the embodiment of FIG. 9, a plurality of resilient fingers or arms 32 extend from the base 18. As they extend from the base, the arms 32 converge, but terminate with ramp portions 33 that diverge. The arms 32 thereby form a grasping attachment which engages the external surfaces of the neck of an ampoule in which the prong 19 is inserted. Typically, the ampoule has a lip adjacent the neck thereof and the arms 32 assist in retaining the ampoule 13 attached to the clip 10 by grasping the neck behind the lip.

In the embodiment of FIG. 10, the portion 19 is split lengthways to form a plurality of resilient arms 34 that are resiliently compressed when inserted in the neck 21.

In the embodiment of FIG. 11, the clip 10 has a C-shaped socket 35 having a longitudinal axis 36 generally normal to the axis 23. The socket 35 is generally arcuate in transverse cross-section and has a side wall 37 that extends generally parallel to the axis 36. The socket 35 is shaped to receive the body 15 and is resiliently urged into contact with the body 15 in a snap fit to releasably attach the clip 10 to the syringe 11. The prong portion 19 is as shown in FIG. 7.

In the embodiment of FIG. 12, the clip of FIG. 9 is modified to include the socket 35 of FIG. 11.

Figure 15:
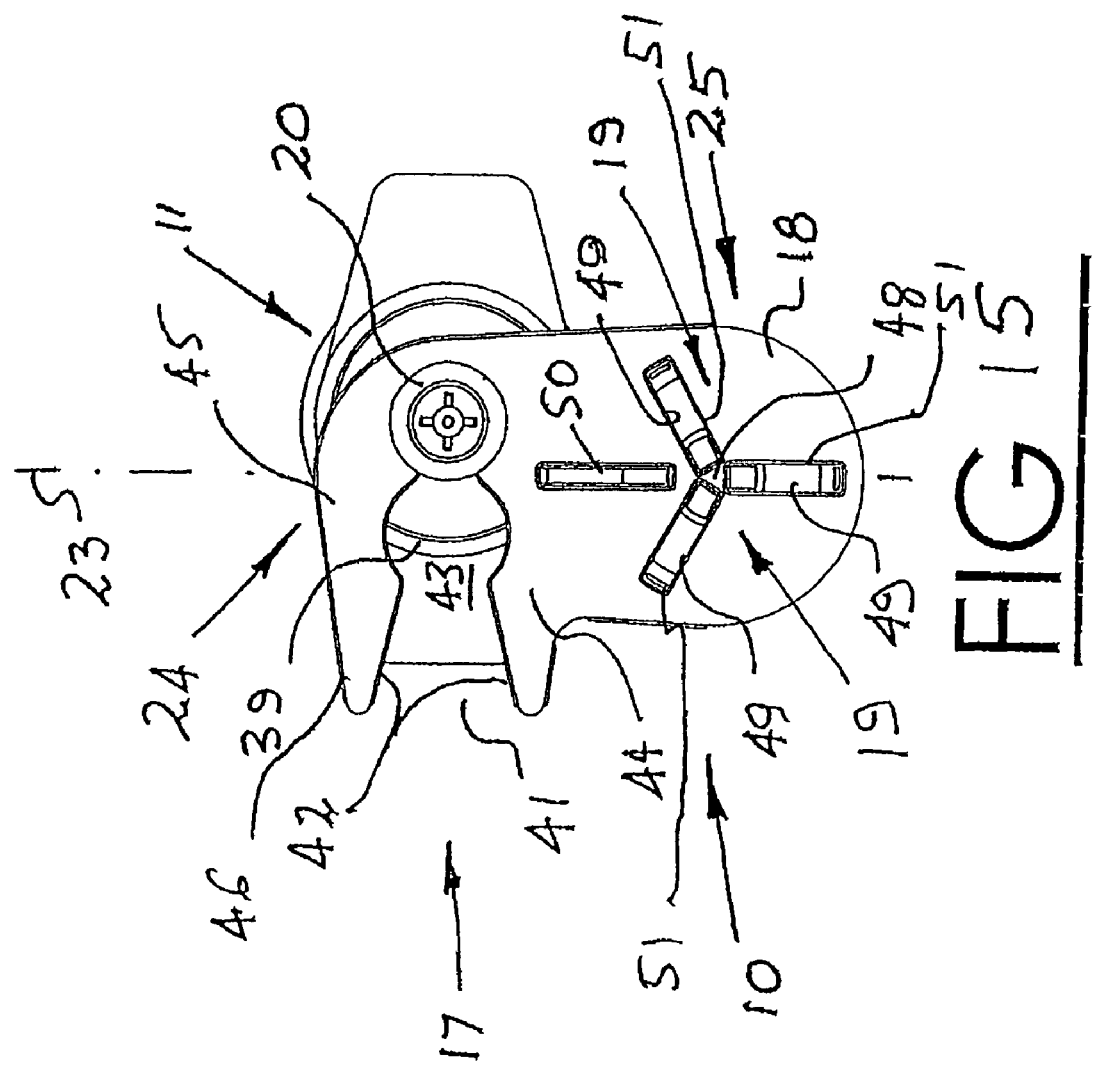
FIG. 15 is an end view of the clip, ampoule and syringe of FIG. 13.
Figure 16:
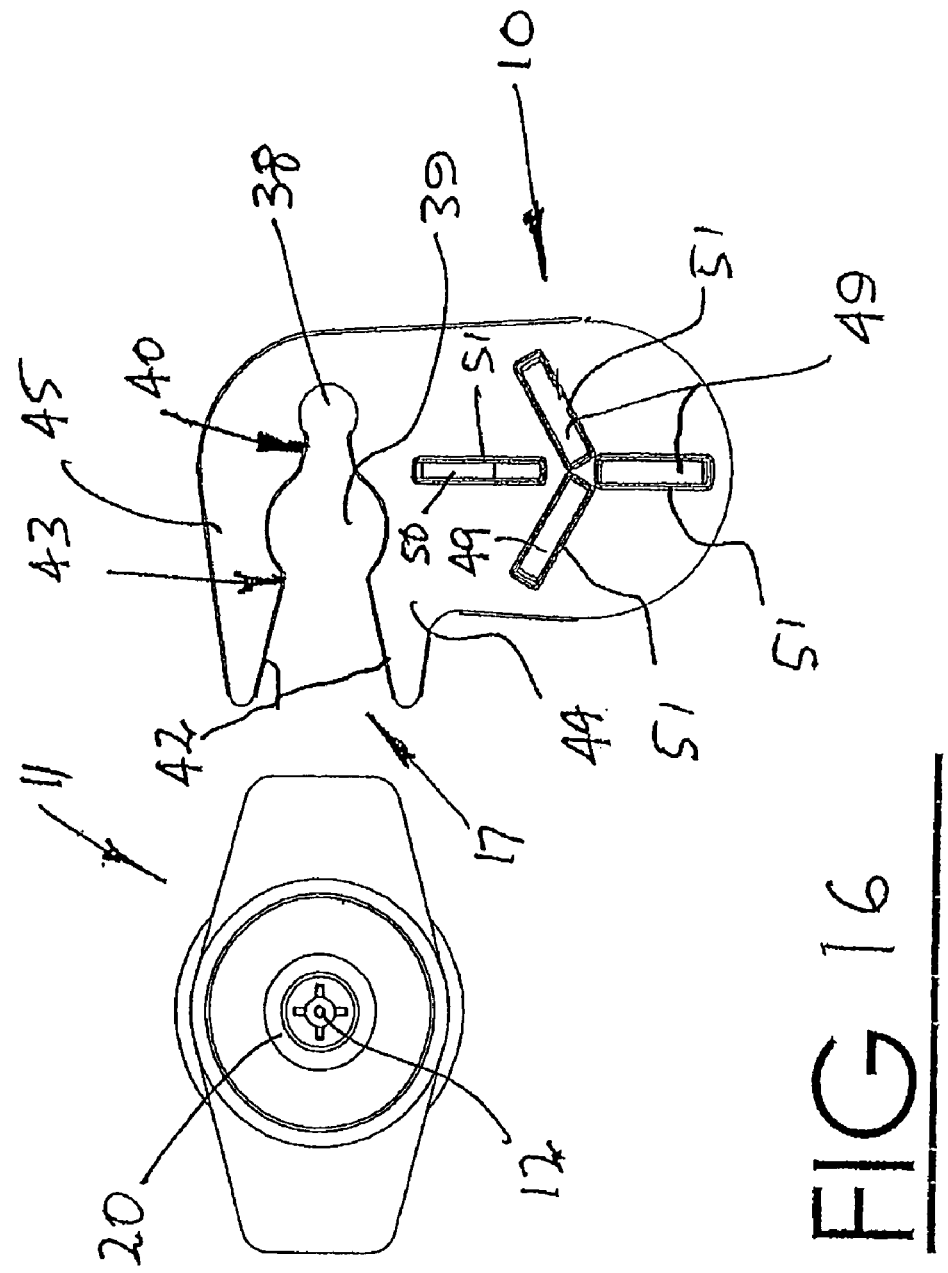
FIG. 16 is an end view of the clip and syringe of FIG. 13 with the clip detached from the syringe.
Figure 17:
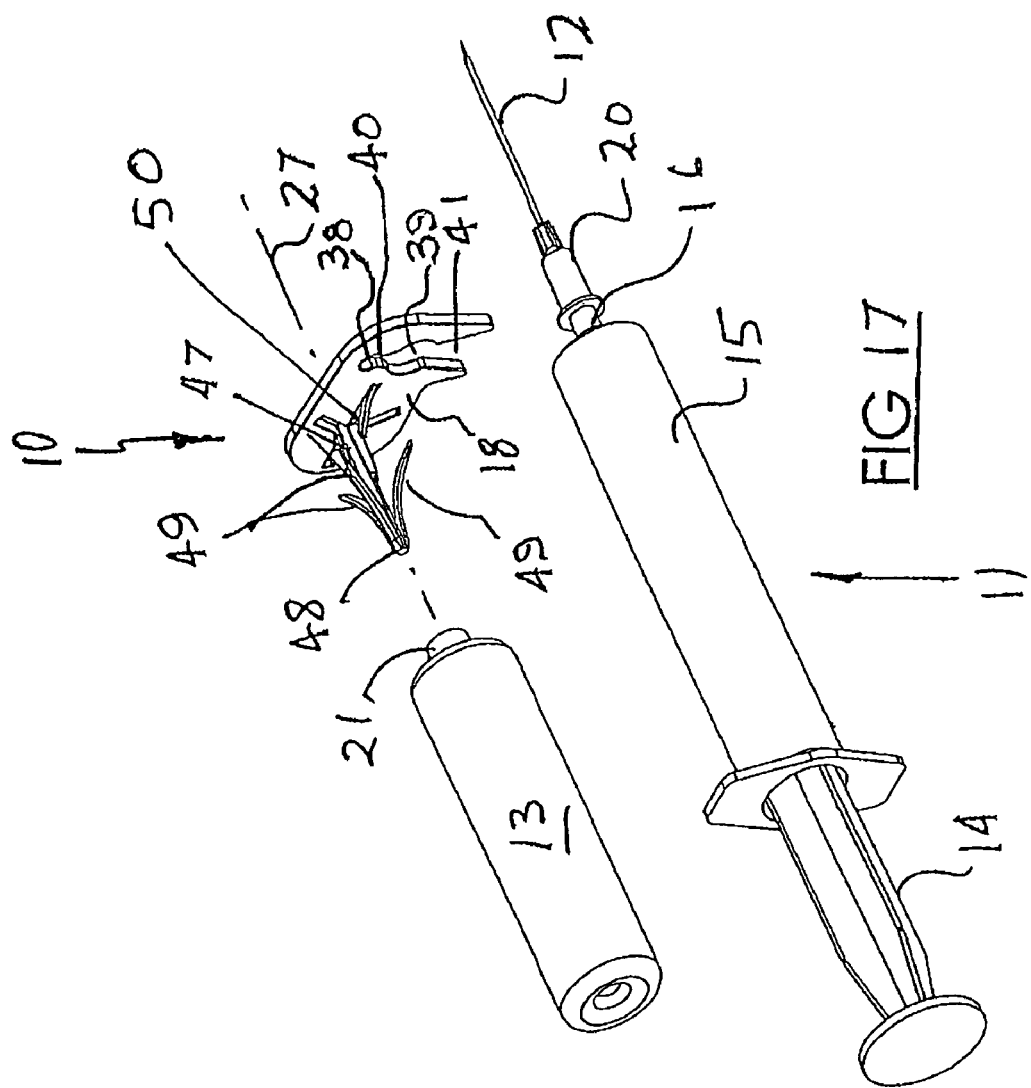
FIG. 17 is an exploded view of the clip, ampoule and syringe of FIG. 13.
Figure 18:
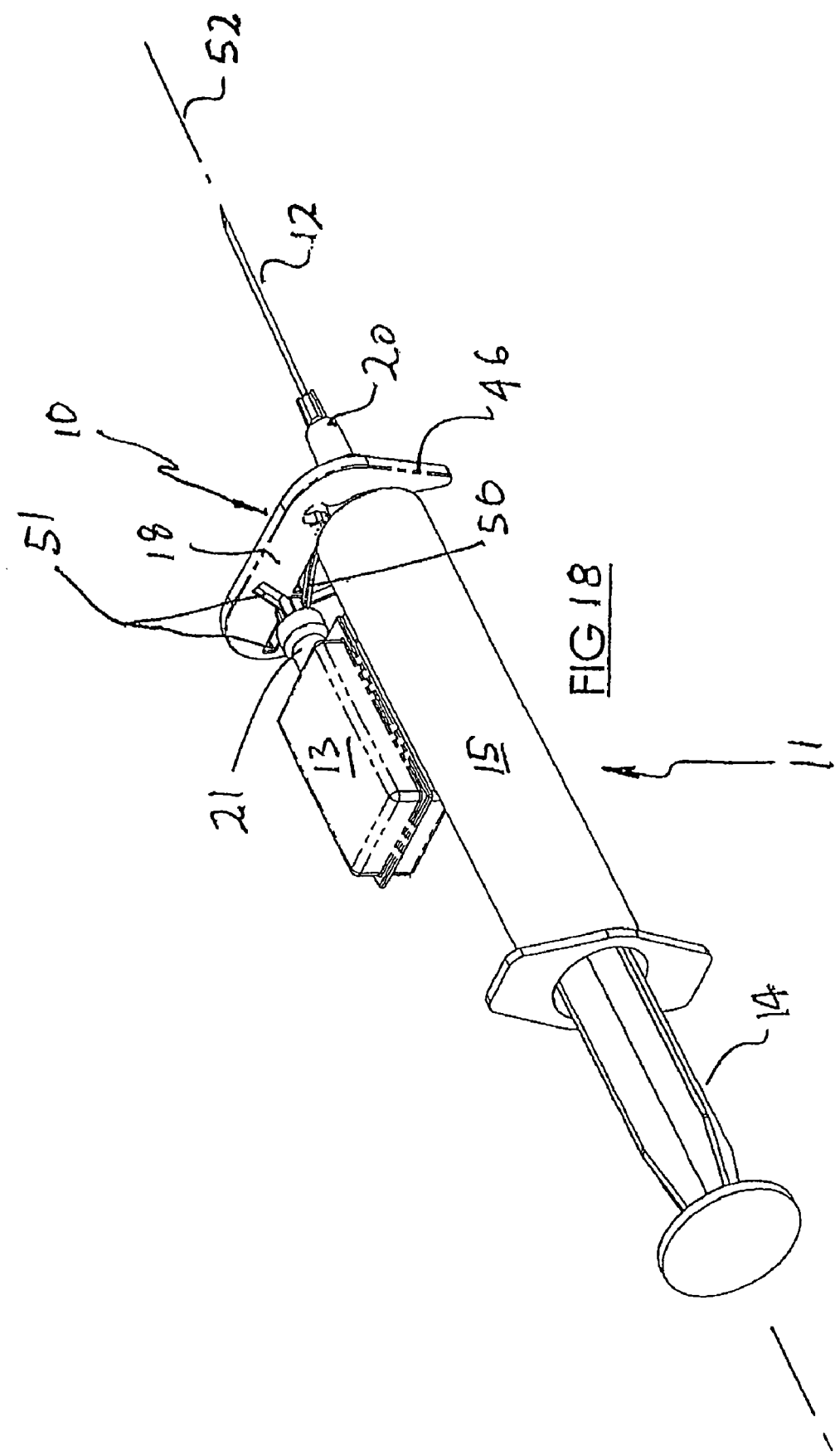
FIG. 18 is an isometric view of the clip and syringe of FIG. 13, with an alternative ampoule.
Figure 19:
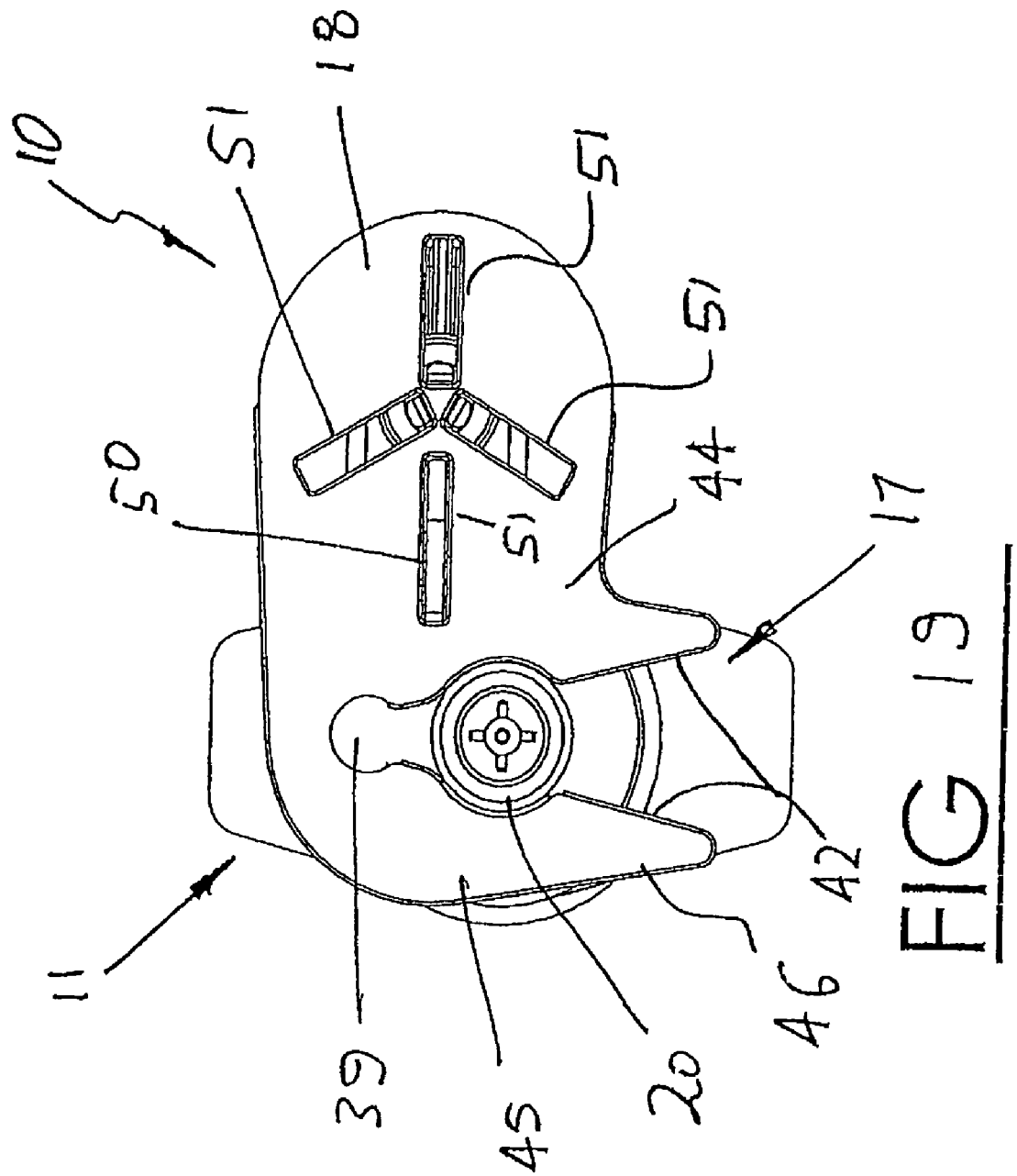
FIG. 19 is an end view of a modification of the clip of FIG. 13, and syringe.

FIGS. 13 to 18 illustrate another embodiment of the invention in which the base 18 of the clip 10 is again provided with a recess 17 which opens in a direction generally normal to the axis 23. As can be seen more clearly in FIG. 16, the recess 17 includes a first or inner portion 38 that communicates with a second or outer portion 39 through a neck portion 40. The second portion 39 communicates with an entrance portion 41 defined by divergent edges 42 of the base 18, via another neck portion 43. The first portion 38 has a narrower transverse width than the second portion 39. As best seen in FIG. 15, the tip 16 can locate snugly in the first portion 38. However, if so required, the needle base 20 can locate snugly in the second portion 39, as seen in FIG. 19.

The recess 17 is located between portions 44 and 45 of the base, with the base portion 45 including an arm 46 that is resiliently deformable to enable entry of the tip 16 or needle base 20 into the recess 17 in a snug or snap fit.

In the embodiment of FIGS. 13 to 18, the ampoule engaging portion 19 includes a finger or stem 47 extending generally normal to the base 18 along the axis 27, to a free end 48. A plurality of extensions, in the form of thin leaves or barbs 49, are formed integrally with the stem 47 and extend from its free end 48 toward the base 18. The barbs 49 diverge as they extend towards the base 18. The barbs 49 are resiliently deformable, so that when inserted into the ampoule neck 21, they are compressed towards the stem 47 as they pass through the neck but then expand radially outwardly once located in the main body of the ampoule 13. The barbs 49 thereby retain the ampoule 13 fixed to the clip 10. The ampoule engaging portion of the clip therefore acts a type of expanding anchor or hook.

Although not necessarily required, the clip 10 may be provided with a resilient leaf or tab 50 that engages the end of the neck 21 to urge the ampoule 13 back against the end extremities of the barbs 49 to hold the ampoule firmly on the clip.

The base 18 includes a plurality of slots 51 for the purposes of tooling, namely to enable tooling to form the barbs 49 and tab 50 from the plastics material of the clip. The barbs 49 in the drawings are visible through the slots 51.

Figure 20:
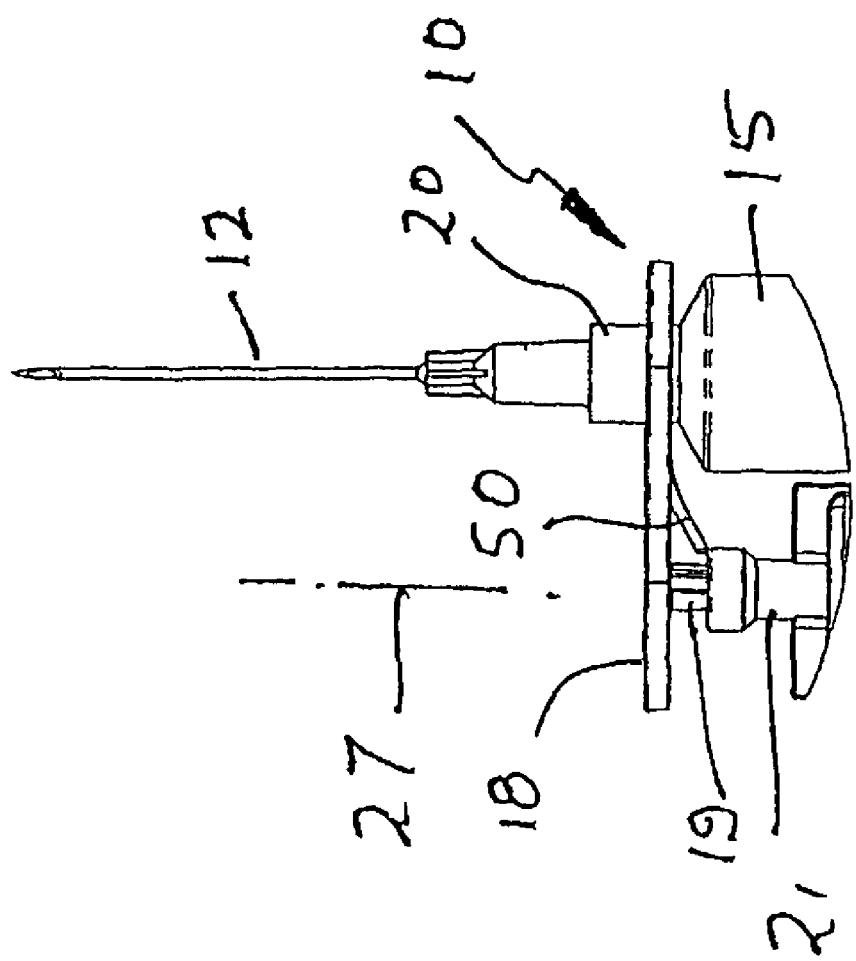
FIG. 20 is a plan view of an end portion of the clip, syringe and ampoule of FIG. 19, illustrating an alternative attachment of the clip to the syringe.
Figure 21:
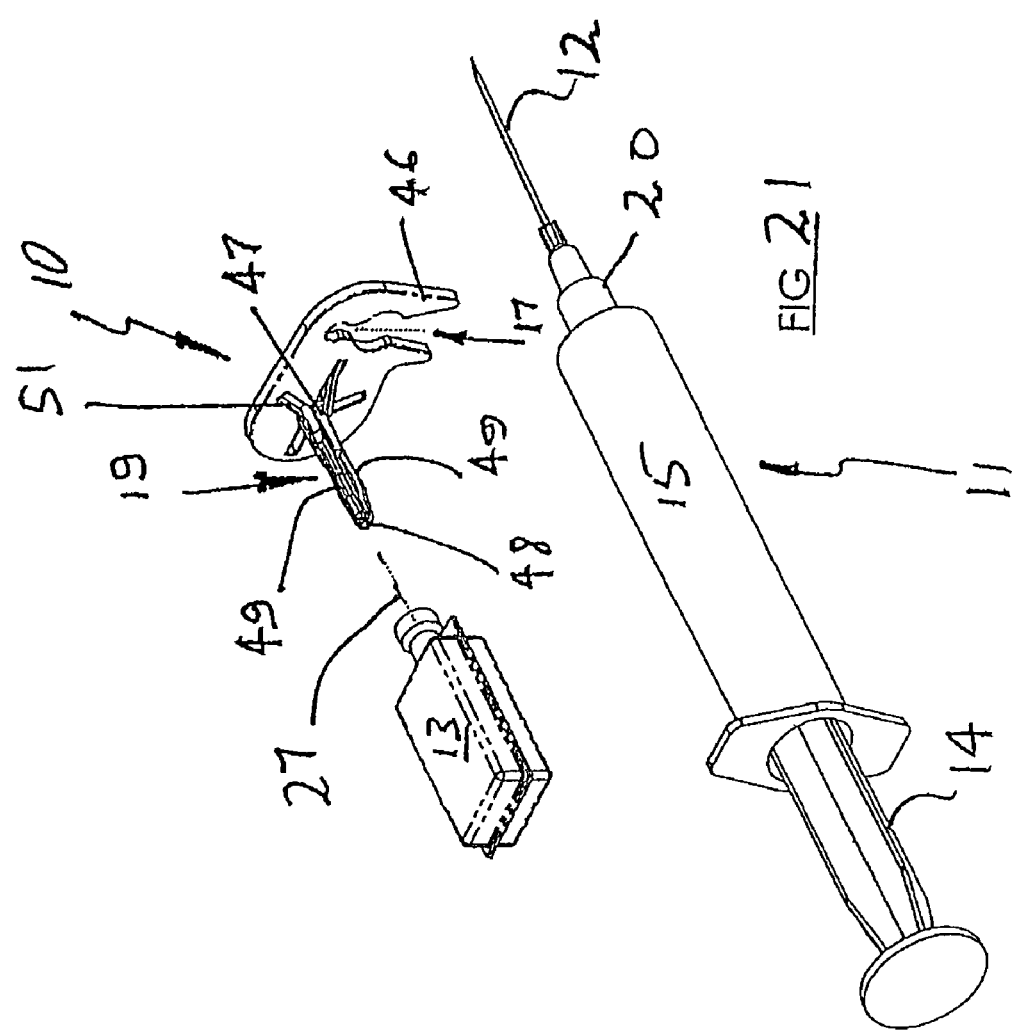
FIG. 21 is an exploded isometric view of the clip, syringe and ampoule of FIG. 18.

In the embodiment of FIGS. 19 to 21, the barbs 49 initially diverge from the free end 48, but then converge back towards the stem 47.

In alternative embodiments, the clip base 18 may be integrally formed with a portion of the syringe 11, such as the needle mounting 20 or syringe body 15. In both these embodiments the base 18 would project laterally relative to the longitudinal axis 53 of the syringe 11, as does the base 18 in the previous embodiments.

Preferred directions for the use of the above medication clip 10 may be as follows:
1. Select appropriate size syringe 11. (1 ml, 2 ml, 5 ml, 10 ml, 20 ml, 50 ml).
2. Select and attach drawing up needle 12/syringe cannula to syringe 11.
3: Apply medication clip 10 to base of tip 16 of syringe 11.
4. Select Drug ampoule/s or vial/s.
5. Draw drug and/or mixing solution in to syringe 11 and connect ampoule/s and vial/s directly onto medication clip 10 (ensuring that ampoule/s and vial/s remains attached to syringe for drug and expiry date confirmation by authorising Medical Officer/Administering Officer).
6. Do not tape ampoule/s onto syringe 11 with medication clip 10. (This practice obscures the Drug name and expiry details which must at all times be legible for correct drug administration/cross checking).
7. When administration complete discard complete unit in appropriate sharps container.

It is to be understood that the terminology employed above is for the purpose of description and should not be regarded as limiting.

The foregoing embodiments are intended to be illustrative of the invention. Accordingly, it is to be understood that the scope of the invention is not limited to the exact construction and operation described and illustrated, but only by the claims.

The invention claimed is:
1. A clip for securing a medication ampoule to a syringe after medication has been drawn from the ampoule into the syringe, said ampoule having an opening in a neck portion thereof, the clip comprising:
   a generally planar base;
   a syringe engaging portion adapted to attach the clip to the exterior of the syringe, the syringe engaging portion comprising:

a recess in the base having an outer opening which is shaped and dimensioned to receive therein, in an interference or snap fit, a cylindrical portion of the syringe, and an inner opening which is smaller than the outer opening and is shaped and dimensioned to receive a reduced-diameter portion of the syringe therein in an interference or snap fit; and an ampoule engaging portion adapted to be received within the opening in the neck portion to hold the ampoule securely on the ampoule engaging portion and thereby attach the ampoule to the clip, the ampoule engaging portion being a projection extending substantially perpendicularly from the base.

2. A clip as claimed in claim 1, wherein the base is made of resiliently flexible plastics material.

3. A clip as claimed in claim 1, wherein the projection has a plurality of resiliently flexible extensions which have a rest configuration wider than the diameter of the opening, whereby upon insertion of the projection through the opening, the extensions are compressed while passing through the neck portion but expand against the inside of the ampoule and wherein the resiliently flexible extensions are affixed to the distal end of the projection, and are spaced circumferentially around the projection.

4. A clip as claimed in claim 1, wherein the syringe engaging portion is adapted to releasably attach the clip to the syringe.

* * * * *